(12) United States Patent
Nomura et al.

(10) Patent No.: US 8,993,603 B2
(45) Date of Patent: Mar. 31, 2015

(54) PHARMACEUTICAL COMPOSITION AND METHOD USING ANTIFUNGAL AGENT IN COMBINATION

(75) Inventors: Nobuhiko Nomura, Toyama (JP); Hiroshi Nishikawa, Toyama (JP); Noritomo Fujino, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 1136 days.

(21) Appl. No.: 11/910,999

(22) PCT Filed: Apr. 5, 2006

(86) PCT No.: PCT/JP2006/307204
§ 371 (c)(1),
(2), (4) Date: Dec. 8, 2008

(87) PCT Pub. No.: WO2006/109642
PCT Pub. Date: Oct. 19, 2006

(65) Prior Publication Data
US 2009/0087480 A1    Apr. 2, 2009

(30) Foreign Application Priority Data
Apr. 7, 2005 (JP) ................................. 2005-110784

(51) Int. Cl.
| | | |
|---|---|---|
| A01N 43/64 | (2006.01) | |
| A61K 31/41 | (2006.01) | |
| A61K 45/06 | (2006.01) | |
| A61K 31/4196 | (2006.01) | |
| A61K 31/445 | (2006.01) | |
| A61K 31/7048 | (2006.01) | |

(52) U.S. Cl.
CPC ............. *A61K 45/06* (2013.01); *A61K 31/4196* (2013.01); *A61K 31/445* (2013.01); *A61K 31/7048* (2013.01)
USPC ................ 514/359; 514/11; 514/31; 514/331

(58) Field of Classification Search
USPC .............................................. 514/11, 31, 331
See application file for complete search history.

(56) References Cited

U.S. PATENT DOCUMENTS 4,348,401 A    9/1982    Friebe et al.

FOREIGN PATENT DOCUMENTS

| EP | 0 026 876 A1 | 4/1981 |
| EP | 1 481 966 A1 | 12/2004 |
| EP | 1 767 526 A1 | 3/2007 |
| JP | 11 504931 | 5/1999 |
| JP | 3288051 | 6/2002 |
| JP | 03 074476 | 9/2003 |
| JP | 2003 527314 | 9/2003 |
| JP | 2005-97298 | 4/2005 |
| WO | 2006 003881 | 1/2006 |

OTHER PUBLICATIONS

Martinez-Irujo et al, Biochemical Pharmacology, vol. 51, pp. 635-644, 1996.*
Antimicrobial Agents and Chemotherapy, vol. 39, p. 1691, 1995.*
Junichi Mitsuyama, et al., "In Vitro and In Vivo Antifungal Activities of T-2307, a Novel Arylamidine", Antimicrobial Agents and Chemotherapy, vol. 52, No. 4, XP-002557123, Apr. 2008, p. 1318-1324.
M. H. Beers, et al., "The Merck Manual",158/ Systemic Fungal Diseases, XP-002557124, 1999, pp. 1209-1213.
U.S. Appl. No. 12/443,750, filed Mar. 31, 2009, Nishikawa.
Kuroda, "Saishin Yakubutsu Ryoho manual—Toyaku no kihon to Chiryo Program—Jokan", Kabushiki Kaisha Nippon Rinshosha, pp. 510-512, III. Chiryoyaku, I Kansen Kagaku Ryoho Ryoiki Ko Shinkin Yaku, 1991.
Sunada, "Miconazole nado Ko Shinkin Yaku no Koboyo Shinkin ni Taisuru in Vitro Heiyo Koka", Japanese Society of Chemotherapy Zasshi, vol. 52, No. 1, pp. 23-30, 2004.

(Continued)

*Primary Examiner* — Wu-Cheng Winston Shen
*Assistant Examiner* — Jean Cornet
(74) *Attorney, Agent, or Firm* — Oblon, McClelland, Maier & Neustadt, L.L.P.

(57) ABSTRACT

A pharmaceutical composition containing one or more antifungal agents selected from an arylamidine derivative represented by the general formula:

[Chemical Formula 1]

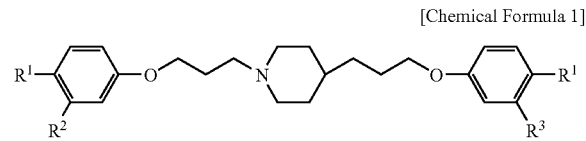

(wherein $R^1$ represents an amidino group that may be substituted with a hydroxyl group that may be protected with an acyl group, an amidino group that may be substituted with an alkoxy group that may be substituted, or an amidino group that may be substituted with an aralkyloxy group that may be substituted; $R^2$ and $R^3$ identically or differently represent a hydrogen atom or a halogen atom) or a salt thereof, an azole antifungal agent, a polyene antifungal agent, a candin antifungal agent and a fluoropyrimidine antifungal agent has a strong antifungal activity and is useful for the treatment of fungal infection. A method for using them in combination is useful as an excellent therapeutic method for fungal infection. A pharmaceutical composition containing the arylamidine derivative represented by the above general formula or a salt thereof and an immunosuppressant has a strong antifungal activity and is useful for the treatment of fungal infection and a skin disease such as atopic dermatitis. A method for using them in combination is useful as an excellent therapeutic method for fungal infection and a skin disease such as atopic dermatitis.

20 Claims, 2 Drawing Sheets

(56) References Cited

OTHER PUBLICATIONS

Niki, "Micafungin to amphotericin B, itraconazole Oyobi fluconazole tono Heiyo Koka", Japanese Society of Chemotherapy Zasshi, vol. 50, No. Supplement-1, pp. 58-67, 2002.
Del Poeta, et al., " Synergistic Antifungal Activities of Bafilomycin $A_1$, Fluconazole, and the Pneumocandin MK-0991/Caspofungin Acetate (L-743,873) with Calcineurin Inhibitors FK506 and L-685,818 against *Cryptococcus neoformans*", Antimicrobial Agents and Chemotherapy, vol. 44, No. 3, pp. 739-746, 2000.
Yamaguchi, "Rinsho to Biseibutsu (Clinics and Microorganisms)", vol. 17, pp. 265-266, 1990.
Mori, Rinsho to Biseibutsu (Clinics and Microorganisms), vol. 21, No. 3, pp. 277-283, 1994.
Ito, et al., Rinsho to Biseibutsu (Clinics and Microorganisms), vol. 30, pp. 595-614, 2003.
Tajima, Nippon Ishinkin Gakkai Zasshi (Japanese Journal of Medical Mycology), vol. 46, pp. 163-167, 2005.
Shinzaisei Shinkinsho no Shindan & Chiryo Gaidorain "(Guidelines for the Diagnosis and Treatment of Deep Mycosis)", (Ishiyaku Pub. Inc.), pp. 20 and 29, 2003.
Sugar, et al., "Interactions of Itraconazole with Amphotericin B in the Treatment of Murine Invasive Candidiasis", The Journal of Infectious Diseases 1988, vol. 177, pp. 1660-1663.
Maesaki, et al., "Effects of Antifungal Agent Combinations Administered simultaneously and Sequentially against *Aspergillus fumigatus*", Antimicrobial Agents and Chemotherapy, Dec. 1994, pp. 2843-2845.

* cited by examiner

PHARMACEUTICAL COMPOSITION AND METHOD USING ANTIFUNGAL AGENT IN COMBINATION

TECHNICAL FIELD

The present invention relates to a pharmaceutical composition which is useful in the treatment of fungal infections caused by fungal pathogens and which comprises an arylamidine derivative or a salt thereof, and one or more agents selected from azole antifungal agents, polyene antifungal agents, candin antifungal agents, fluoropyrimidine antifungal agents and immunosuppressants. The present invention also relates to a method for combination use of the agents to treat fungal infections.

BACKGROUND ART

Serious deep mycosis such as invasive candidiasis can often be a fatal disease. In the past, it has been considered that the principal protective mechanism on the side of a host organism against fungi such as *Candida* is nonspecific immunization by neutrophils. When this protective mechanism functions normally there is little risk of becoming infected with fungi. However, in recent years, the risk of suffering from deep mycosis has been boosted because of the increased number of patients with underlying diseases decreasing the immunological function of the body, such as malignant tumors (in particular, hemopoietic malignant tumors such as acute leukemia or malignant lymphoma) and AIDS, frequent use of anticancer agents or immunosuppressants, heavy use of antibacterial antibiotics or steroid hormones, long-term use of central venous hyperalimentation or venous catheterization and the like (Non-Patent Document 1).

Agents used for the treatment of such deep mycosis are very few, when compared to antibacterial agents used, and include only amphotericin B, flucytosine, miconazole, fluconazole, itraconazole, voriconazole, micafungin and the like.

Accordingly, there is an increasing need for safe and effective agents against opportunistic fungal infections caused by fungal pathogens such as *Candida*, *Cryptococcus* and *Aspergillus*.

While the agents that are used at present, for example, amphotericin B, have an extremely strong fungicidal action, they have a problem regarding side effects such as nephrotoxicity, so that their clinical usage is limited. It is rare at present that flucytosine is used singly because this agent has problems with, for example, development of resistance. Micafungin has a low activity against the *Cryptococcus*. Azoles such as fluconazole and voriconazole are most frequently used at present due to their balance between effectiveness and safety, although their fungicidal action is inferior to that of amphotericin B (Non-Patent Documents 2 and 3).

*Malassezia*, which is a pathogenic fungus of superficial fungal infections, is a fungal pathogen which is thought to be a cause or exacerbating factor in skin diseases such as tinea versicolor, seborrheic dermatitis and atopic dermatitis. Therefore, using antifungal agents for the treatment of these diseases would be effective. However, antifungal agents having excellent antifungal activity against *Malassezia* are limited to just a few antifungal agents such as ketoconazole and itraconazole. In addition, there have been reports of renewed outbreaks once treatment has finished, meaning that satisfactory treatment effects cannot be guaranteed (Non-Patent Document 4).

Methods for combination use of antifungal agents are being used for purposes such as to boost treatment effects (Non-Patent Document 5). Research is also progressing into the combination of antifungal agents (Patent Documents 1, 2 and 3). However, the number of agents being combined is limited, meaning that satisfactory treatment effects cannot be guaranteed.

On the other hand, arylamidine derivatives having antifungal activity are known (Patent Document 4).

Patent Document 1: Japanese Patent No. 3288051
Patent Document 2: JP-A-11-504931
Patent Document 3: JP-A-2003-527314
Patent Document 4: International Patent Publication No. WO03/074476
Non-Patent Document 1: Rinsho to Biseibutsu (Clinics and Microorganisms), Vol. 17, pp. 265-266, 1990
Non-Patent Document 2: Rinsho to Biseibutsu (Clinics and Microorganisms), Vol. 21, pp. 277-283, 1994
Non-Patent Document 3: Rinsho to Biseibutsu (Clinics and Microorganisms), Vol. 30, pp. 595-614, 2003
Non-Patent Document 4: Nippon Ishinkin Gakkai Zasshi (Japanese Journal of Medical Mycology), Vol. 46, pp. 163-167, 2005
Non-Patent Document 5: Shinzaisei Shinkinsho no Shindan & Chiryo Gaidorain (Guidelines for the Diagnosis and Treatment of Deep Mycosis), p. 20, p. 29, 2003 (Ishiyaku Pub. Inc.)

DISCLOSURE OF THE INVENTION

Desirable are a pharmaceutical composition which is useful in treating fungal infections and which has strong antifungal activity yet few side effects, and a method for combination use of antifungal agents.

Under such circumstances, as a result of intensive study, the present inventors discovered that a pharmaceutical composition comprising an arylamidine derivative or a salt thereof, represented by the following general formula [1]:

[Formula 1]

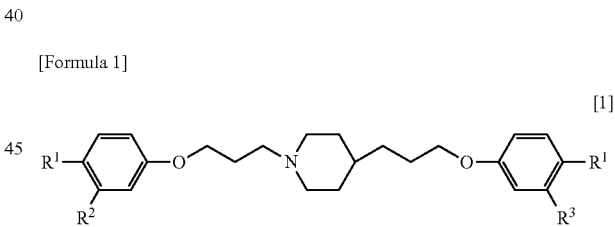

[1]

wherein $R^1$ represents an amidino group which may be substituted with a hydroxyl group which may be protected with an acyl group, an amidino group which may be substituted with an alkoxy group which may be substituted, or an amidino group which may be substituted with an aralkyloxy group which may be substituted; and $R^2$ and $R^3$ may be the same or different, and represent a hydrogen atom or a halogen atom; and one or more antifungal agents selected from azole antifungal agents, polyene antifungal agents, candin antifungal agents and fluoropyrimidine antifungal agents, has a strong antifungal activity and is useful in treating fungal infections, and that a method for combination use of these antifungal agents is useful in treating fungal infections, thereby arriving at the present invention.

In addition, the present inventors found that a pharmaceutical composition comprising the arylamidine derivative represented by general formula [1] or a salt thereof and immunosuppressants has a strong antifungal activity and is useful in treating fungal infections and skin diseases such as atopic dermatitis, and that a method for combination use of these agents is useful in treating fungal infections and skin diseases such as atopic dermatitis, thereby arriving at the present invention.

The pharmaceutical composition comprising the arylamidine derivative or a salt thereof having an antifungal activity, and one or more antifungal agents selected from azole antifungal agents, polyene antifungal agents, candin antifungal agents and fluoropyrimidine antifungal agents, has a strong antifungal activity and is useful in treating fungal infections. A method for combination use of these antifungal agents is useful as an excellent treatment method of fungal infections.

Further, the pharmaceutical composition comprising the arylamidine derivative or the salt thereof and immunosuppressants has a strong antifungal activity and is useful in treating fungal infections and skin diseases such as atopic dermatitis. A method for combination use of these agents is useful in treating fungal infections and skin diseases such as atopic dermatitis.

BEST MODE FOR CARRYING OUT THE INVENTION

The present invention will now be described in more detail.

In the present specification, unless otherwise noted, a halogen atom refers to a fluorine atom, a chlorine atom, a bromine atom, or an iodine atom; an alkyl group, for example, refers to a straight or branched $C_{1-12}$ alkyl group such as methyl, ethyl, propyl, isopropyl, butyl, sec-butyl, isobutyl, tert-butyl, pentyl, isopentyl, hexyl, heptyl, and octyl; a lower alkyl group, for example, refers to a straight or branched $C_{1-6}$ alkyl group such as methyl, ethyl, propyl, isopropyl, butyl, sec-butyl, isobutyl, tert-butyl, pentyl, and isopentyl; an alkenyl group, for example, refers to a straight or branched $C_{2-12}$ alkenyl group such as vinyl, allyl, propenyl, isopropenyl, butenyl, isobutenyl, pentenyl, hexenyl, heptenyl, and octenyl; an aryl group, for example, refers to a group such as phenyl and naphthyl; an aralkyl group, for example, refers to an ar$C_{1-6}$-alkyl group such as benzyl, diphenylmethyl, trityl, phenethyl, and naphthylmethyl;

an alkoxy group, for example, refers to a straight or branched $C_{1-6}$ alkyloxy group such as methoxy, ethoxy, propoxy, isopropoxy, butoxy, isobutoxy, sec-butoxy, tert-butoxy, pentyloxy, and isopentyloxy; an aralkyloxy group, for example, refers to an ar-$C_{1-6}$-alkyloxy group such as benzyloxy, diphenylmethyloxy, trityloxy, phenethyloxy, and naphthylmethyloxy; an alkoxyalkyl group, for example, refers to a $C_{1-6}$-alkyloxy-$C_{1-6}$-alkyl group such as methoxymethyl and 1-ethoxyethyl; an aralkyloxyalkyl group, for example, refers to an ar-$C_{1-6}$-alkyloxy-$C_{1-6}$-alkyl group such as benzyloxymethyl and phenethyloxymethyl;

an acyl group, for example, refers to a formyl group, a straight or branched $C_{2-12}$ alkanoyl group such as an acetyl, propionyl, and isovaleryl, an ar-$C_{1-6}$-alkylcarbonyl group such as benzylcarbonyl, an aroyl group such as benzoyl and naphthoyl, a heterocyclic carbonyl group such as nicotinoyl, thenoyl, pyrrolidinocarbonyl, and furoyl, a succinyl group, a glutaryl group, a maleoyl group, a phthaloyl group, or a straight or branched α-aminoalkanoyl group whose N-terminal may be protected, derived from an amino acid (including, for example, glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline, or hydroxyproline);

an alkyloxycarbonyl group, for example, refers to a straight or branched $C_{1-12}$ alkyloxycarbonyl group such as methoxycarbonyl, ethoxycarbonyl, 1,1-dimethylpropoxycarbonyl, isopropoxycarbonyl, 2-ethylhexyloxycarbonyl, tert-butoxycarbonyl, and tert-pentyloxycarbonyl; an aralkyloxycarbonyl group, for example, refers to an ar-$C_{1-6}$-alkyloxycarbonyl group such as benzyloxycarbonyl and phenethyloxycarbonyl group; an aryloxycarbonyl group, for example, refers to a group such as phenyloxycarbonyl; a heterocyclic oxycarbonyl group, for example, refers to a group such as 2-furfuryloxycarbonyl and 8-quinolyloxycarbonyl;

an arylthio group, for example, refers to a group such as phenylthio; an alkanesulfonyl group, for example, refers to a $C_{1-6}$ alkanesulfonyl group such as methanesulfonyl, ethanesulfonyl, and propanesulfonyl; an arylsulfonyl group, for example, refers to a group such as benzenesulfonyl, toluenesulfonyl, and naphthalenesulfonyl; an aralkylidene group, for example, refers to a group such as benzylidene and naphthylmethylene; a cycloalkylidene group, for example, refers to a group such as cyclopentylidene and cyclohexylidene; a dialkylaminoalkylidene group, for example, refers to a group such as N,N-dimethylaminomethylene and N,N-diethylaminomethylene; a nitrogen-containing heterocyclic alkylidene group, for example, refers to a group such as 3-hydroxy-4-pyridylmethylene;

an oxygen-containing heterocyclic alkyl group, for example, refers to a group such as 5-methyl-2-oxo-2H-1,3-dioxol-4-ylmethyl; an oxygen-containing heterocyclic group, for example, refers to a group such as tetrahydrofuryl and tetrahydropyranyl; a sulfur-containing heterocyclic group, for example, refers to a group such as tetrahydrothiopyranyl; a diarylphosphoryl group, for example, refers to a group such as diphenylphosphoryl; a diaralkylphosphoryl group, for example, refers to a group such as dibenzylphosphoryl; and a substituted silyl group, for example, refers to a group such as trimethylsilyl, triethylsilyl, and tributylsilyl.

Each of the above-described groups may be further substituted with one or more groups selected from a halogen atom, an amino group which may be protected, a hydroxyl group which may be protected, a nitro group, a lower alkyl group, an alkenyl group, an alkoxy group, an aralkyloxy group, an aryl group, an acyl group, and an oxo group.

The amino-protecting groups encompass all of the conventional groups which can be used as protective groups for an amino group, and include, for example, an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkanesulfonyl group, an arylsulfonyl group, an aralkylidene group, a cycloalkylidene group, a dialkylaminoalkylidene group, a nitrogen-containing heterocyclic alkylidene group, an oxygen-containing heterocyclic alkyl group, a diarylphosphoryl group, a diaralkylphosphoryl group and a substituted silyl group.

The hydroxyl-protecting groups encompass all of the conventional groups which can be used as protective groups for a hydroxyl group, and include, for example, an acyl group, an alkyloxycarbonyl group, an aralkyloxycarbonyl group, a heterocyclic oxycarbonyl group, an alkyl group, an alkenyl group, an aralkyl group, an oxygen-containing heterocyclic group, a sulfur-containing heterocyclic group, an alkoxyalkyl group, an aralkyloxyalkyl group, an alkanesulfonyl group, an arylsulfonyl group and a substituted silyl group.

Examples of the compound represented by general formula [1] used in the present invention include the following.

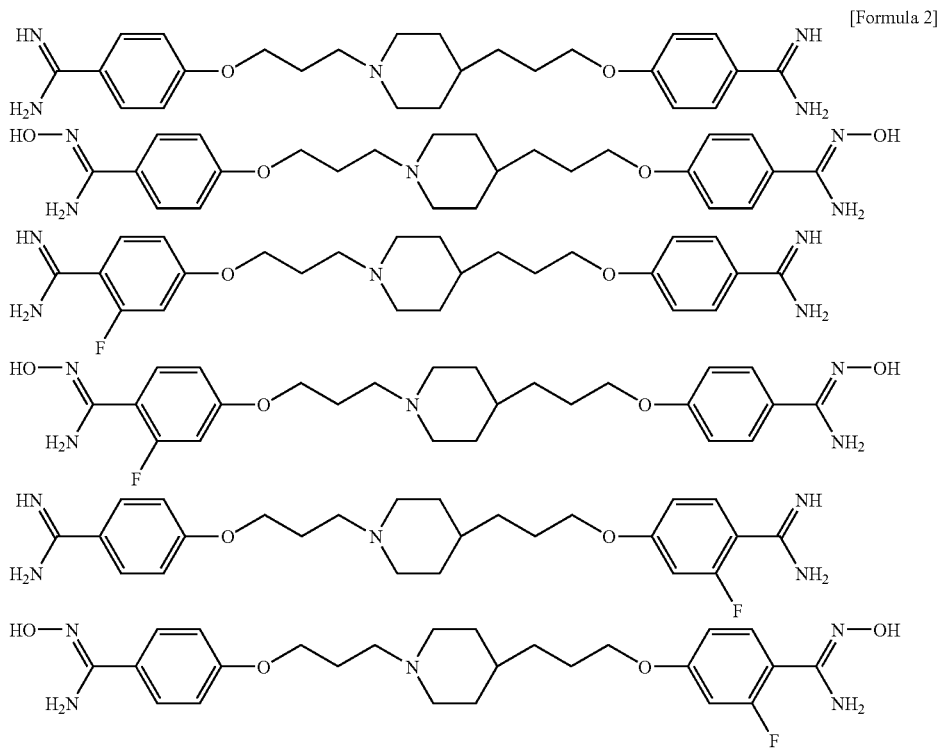

[Formula 2]

For the present compound, preferred examples of the compounds represented by general formula [1] include the following.

As the compound represented by general formula [1], compounds in which $R^1$ is an amidino group which may be substituted with a hydroxyl group are preferred, and compounds in which $R^1$ is an amidino group are more preferred.

Compounds in which $R^2$ and $R^3$ are a hydrogen atom are preferred.

Specifically, as the compound represented by general formula [1], the following compounds are even more preferred.

For the compound represented by general formula [1] or the salt thereof, in cases where the solvate or hydrate exists, such solvate or hydrate can be used. Further, crystals having a variety of shapes may also be used.

Examples of the salts of the compound represented by general formula [1] include the salts of mineral acids, such as hydrochloric acid, hydrobromic acid and sulfuric acid; the salts of organic carboxylic acids, such as tartaric acid, formic acid, acetic acid, citric acid, trichloroacetic acid and trifluoroacetic acid; the salts of sulfonic acids such as methanesulfonic acid, benzenesulfonic acid, p-toluenesulfonic acid, mesitylenesulfonic acid and naphthalenesulfonic acid; and the salts of phosphoric acid.

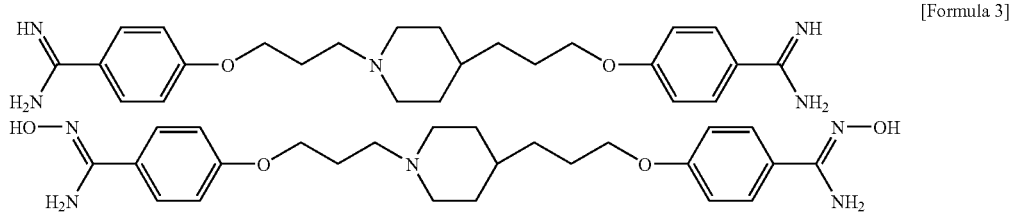

[Formula 3]

As the compound represented by general formula [1], the following compounds are even more preferred.

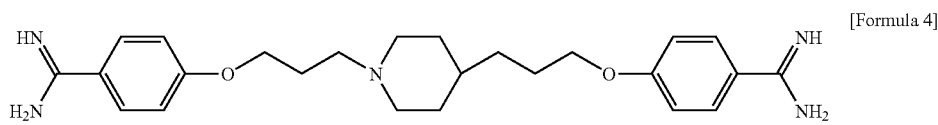

[Formula 4]

Preferred salts of the compound represented by general formula [1] include pharmacologically acceptable salts, and hydrochloride salts are more preferred.

Although the compound of general formula [1] used in the present invention may be produced by conventional methods, it can also be produced by the methods described in, for example, International Patent Publication No. WO2006/003881 pamphlet.

Examples of the azole antifungal agents used in the present invention include triazole antifungal agents, such as fluconazole, fosfluconazole, itraconazole, voriconazole, posaconazole, ravuconazole, BMS-379224, BAL-8557 and CS-758, as well as imidazole antifungal agents, such as ketoconazole, miconazole, bifonazole, lanoconazole and luliconazole.

Preferred examples of the azole antifungal agents include triazole antifungal agents, such as fluconazole, fosfluconazole, itraconazole, voriconazole, posaconazole, ravuconazole, BMS-379224, BAL-8557 and CS-758. More preferred are fluconazole, fosfluconazole, voriconazole and itraconazole, and even more preferred are fluconazole, voriconazole and itraconazole.

Examples of the polyene antifungal agents used in the present invention include amphotericin B and liposomal formulations thereof (e.g., Abelcet (trade name) or AmBisome (trade name)), nystatin, trichomycin, SPK-843 and pimaricin.

Preferred examples of the polyene antifungal agents include amphotericin B and liposomal formulations thereof (e.g., Abelcet (trade name) or AmBisome (trade name)).

Examples of the candin antifungal agents used in the present invention include micafungin, caspofungin, anidulafungin and aminocandin.

Preferred examples of the candin antifungal agents used in the present invention include micafungin.

Examples of the fluoropyrimidine antifungal agents used in the present invention include flucytosine.

Examples of the immunosuppressants used in the present invention include macrolide compounds, such as rapamycin, cyclosporine and tacrolimus.

Preferred examples of the immunosuppressants include tacrolimus.

The administration route of the arylamidine derivative or the salt thereof represented by general formula [1] is not especially limited, and the arylamidine derivative or the salt thereof can be administered intravenously, orally, intramuscularly, subcutaneously or by some other administration route. Further, the arylamidine derivative or the salt thereof represented by general formula [1] can also be administered simultaneously, separately, or in a specific order, with the azole antifungal agents, polyene antifungal agents, candin antifungal agents, fluoropyrimidine antifungal agents and immunosuppressants.

The pharmaceutical composition according to the present invention exhibits excellent action against fungi such as *Candida, Cryptococcus, Aspergillus* and *Malassezia*. The pharmaceutical composition according to the present invention exhibits especially excellent action against *Candida* such as *Candida albicans, Candida glabrata, Candida guilliermondii, Candida kefyr, Candida krusei, Candida parapsilosis, Candida stellatoidea, Candida tropicalis* and *Candida lusitaniae; Cryptococcus* such as *Cryptococcus neoformans; Aspergillus* such as *Aspergillus clavatus, Aspergillus flavus, Aspergillus fumigatus, Aspergillus nidulans, Aspergillus niger, Aspergillus terreus, Aspergillus versicolor* and *Aspergillus restrictus*; and *Malassezia* such as *Malassezia furfur, Malassezia pachydermatis, Malassezia sympodialis* and *Malassezia slooffiae*.

The pharmaceutical composition according to the present invention is effective in the prevention and treatment of a variety of fungal infections, such as candidosis, cryptococcosis, aspergillosis and malasseziasis.

With the pharmaceutical composition according to the present invention, more serious fungal infections can be treated. In addition, since a strong antifungal action is exhibited even if the amount of each of the agents that are administered is lowered, the side effects of the respective agents can be reduced.

Further, a pharmaceutical composition which contains the immunosuppressant agents exhibits excellent effects against superficial fungi such as *Malassezia*, which is thought to be one cause or exacerbating factor in skin disorders such as atopic dermatitis. In addition, the immunosuppressants, which are a component of the pharmaceutical composition, exhibit an effect against skin disorders such as atopic dermatitis. Therefore, a pharmaceutical composition which contains the immunosuppressants is useful as a pharmaceutical composition for antifungal treatment and for skin disorder treatment against atopic dermatitis or the like.

EXAMPLES

The present invention will now be described in more detail with reference to the following Test Examples. However, the present invention is not limited to these examples.

The respective abbreviations have the following meaning. FLCZ: fluconazole; MCFG: micatungin; AMPH-B: amphotericin B; ITCZ: itraconazole; 5-FC: flucytosine; VLCZ: voriconazole; KCZ: ketoconazole; and TAC: tacrolimus.

The following compound was selected as the Test Compound. The chemical structural formula of this compound is illustrated below.

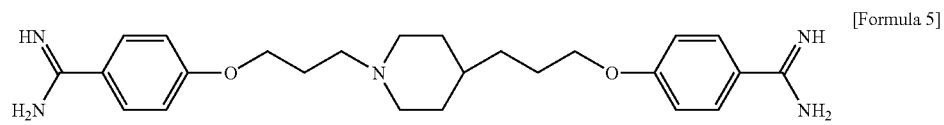

[Formula 5]

Selected as the agents were fluconazole (commercially-available product), micafungin (commercially-available product), amphotericin B (commercially-available product), itraconazole (commercially-available product), voriconazole (commercially-available product), ketoconazole (commercially-available product), tacrolimus (commercially-available product) and flucytosine (Sigma).

Test Example 1

In Vitro Test (*Aspergillus* and *Cryptococcus*)

Susceptibility testing of fungi was carried out using a broth dilution method.

The medium used in the susceptibility test consisted of RPMI1640 (Sigma) (RPMI/MOPS) adjusted to a pH of 7.0 with 0.165 mol/L morpholinepropanesulfonic acid (MOPS) and 1.0 mol/L sodium hydroxide.

The test compound was dissolved in a small amount of 0.1 mol/L hydrochloric acid. The solution was diluted with sterile water, and then prepared to a predetermined concentration using RPMI/MOPS.

The agents were dissolved in a small amount of sterile water or dimethylsulfoxide, and the resultant solutions were then prepared to a predetermined concentration using RPMI/MOPS.

Each inoculum was prepared by diluting a suspension of *Cryptococcus neoformans* ATCC90112 that had been cultured for two nights at 35° C. on a Sabouraud agar plate or by diluting a conidia suspension of *Aspergillus fumigatus* TIMM0063 suspended in sterile physiological saline solution to a predetermined concentration using RPMI/MOPS (final concentration for each solution: approximately $1 \times 10^3$ cells/mL and approximately $1 \times 10^4$ CFU/mL). Finally, a microplate was made containing the predetermined concentrations of the test compound and the respective agents, as well as the medium and the fungi. The plate was cultured at 35° C. for 48 to 72 hours. Absorbance at 630 nm was measured before and after cultivation using an automatic spectrophotometer. The lowest concentration at which 50% growth inhibition was observed as compared to a growth control where no test substance was added was defined as $IC_{50}$.

A FIC index was calculated by comparing the $IC_{50}$ for the test compound with those for fluconazole, micafungin, amphotericin B, itraconazole and flucytosine when used singly and when used in combination, and evaluating the antifungal activity of the respective agent combination with the test compound by a checkerboard method. The FIC index takes the minimum value of the values determined according to: ($IC_{50}$ value when used in combination with the test compound/$IC_{50}$ value when used singly with the test compound)+ ($IC_{50}$ value when used in combination with the agent/$IC_{50}$ value when used singly with the agent).

In cases where the FIC index was 0.5 or less, it was determined that there was a strong synergistic effect as a result of the combination of both agents (Antimicrobial Agents and Chemotherapy, Vol. 39, p. 1691, 1995).

The results of the combination of the test compound with the respective agents against *Aspergillus fumigatus* TIMM0063 are shown in Table 1.

TABLE 1

| Composition | Test Compound MCFG | Test Compound AMPH-B | Test Compound 5-FC |
|---|---|---|---|
| FIC index | 0.31 | 0.25 | ≤0.14 |

A strong synergistic effect was confirmed for the test compound with micafungin, amphotericin B and flucytosine.

The results of the combination of the test compound with the respective agents against *Cryptococcus neoformans* ATCC90112 are shown in Table 2.

TABLE 2

| Composition | Test Compound FLCZ | Test Compound ITCZ | Test Compound AMPH-B | Test Compound 5-FC |
|---|---|---|---|---|
| FIC index | 0.31 | 0.38 | 0.38 | 0.38 |

A strong synergistic effect was confirmed for the test compound with fluconazole, itraconazole, amphotericin B and flucytosine.

Test Example 2

In Vitro Test (*Malassezia*)

Susceptibility testing of fungi was carried out using a broth dilution method.

The medium used in the susceptibility test consisted of a mixture (m RPMI/MOPS) of RPMI1640 (Sigma) adjusted to a pH of 7.0 with 0.165 mol/L 3-(N-morpholino)propanesulfonic acid (MOPS) and 1.0 mol/L sodium hydroxide, glucose, ox bile, glycerol and Tween 20 (Wako Pure Chemical Industries, Ltd.).

The test compound was dissolved in a small amount of 0.1 mol/L hydrochloric acid. The solution was diluted with sterile water, and then prepared to a predetermined concentration using m RPMI/MOPS. Itraconazole, ketoconazole and tacrolimus were dissolved in dimethylsulfoxide, and the resultant solutions were then prepared to a predetermined concentration using m RPMI/MOPS.

An inoculum was prepared by suspending *Malassezia furfur* NBRC0656 that had been cultured for two nights at 30° C. on a 103 agar medium (a medium formed by preparing a mixture of 1% glucose, 0.5% peptone, 0.3% yeast extract and 0.3% malt extract to a pH of 5.6 using 1.0 mol/L hydrochloric acid, charging the mixture with 1% olive oil and 1.5% agar powder and then subjecting the resultant mixture to high-pressure steam sterilization) to a predetermined concentration using m RPMI/MOPS (final concentration for the solution: approximately $1 \times 10^3$ cells/mL). Finally, a microplate was made containing the predetermined concentrations of the test compound, the respective agents, the medium and the fungi. The plate was cultured at 30° C. for 70 to 72 hours.

The lowest concentration at which fungi growth was not observed after cultivation had finished was defined as the MIC.

A FIC index was calculated by comparing the MIC for the test compound with that for the itraconazole, ketoconazole and tacrolimus when used singly and when used in combination, and evaluating the antifungal activity of the respective agent combination with the test compound by a checkerboard method. The FIC index takes the minimum value of the values determined according to: (MIC value when used in combination with the test compound/MIC value when used singly with the test compound)+(MIC value when used in combination with the agent/MIC value when used singly with the agent).

The results of the combination of the test compound with the respective agents against *Malassezia furfur* NBRC0656 are shown in Table 3.

TABLE 3

| Composition | Test Compound ITCZ | Test Compound KCZ | Test Compound TAC |
|---|---|---|---|
| FIC index | 0.49 | 0.48 | ≤0.43 |

A strong synergistic effect was confirmed for the test compound with itraconazole, ketoconazole and tacrolimus.

Test Example 3

In Vivo Test (*Candida*)

In vivo activity was evaluated by employing a mouse systemic infection model using *Candida albicans*.

Mice (four-week old (at infection) male ICR mice, 10 mice per group) were intraperitoneally administered with cyclophosphamide 4 days prior to infection (200 mg/kg) and the day after infection (100 mg/kg). An inoculum was prepared by suspending *Candida albicans* TIMM1623 on a Sabouraud agar plate that had been cultured for one night at 35° C. in sterile physiological saline solution, counting the number of cells using a biological microscope, and then diluting with sterile physiological saline solution. The mice were intravenously inoculated in their tails with 0.2 mL of the inoculum to induce infection (approximately $3 \times 10^4$ CFU/mouse).

The test compound was dissolved in a small amount of 0.1 mol/L hydrochloric acid, and the resultant solution was diluted with sterile physiological saline solution.

Fluconazole and micafungin were prepared using sterile physiological saline solution.

Amphotericin B was dissolved in 5% glucose.

The test compound (0.0313 mg/kg), fluconazole (0.25 mg/kg), amphotericin B (0.1 mg/kg) and micafungin (0.25 mg/kg) were subcutaneously administered 2 hours after infection and then once a day for 6 days for a total of 7 times. The test was carried out for the case where each of the agents was administered singly and in combination by administering each of the agents immediately after the test compound had been administered.

The survival time for the groups where the test compound or each of the agents was administered singly, and the survival time for the groups where the test compound was administered in combination with each of the agents, were tested to determine whether there was any significant difference at the 5% two-sided significance level with respect to the survival time of a group not administered with any agents using the Kaplan-Meier log rank test (multiple group comparison). The test results are shown in FIGS. 1 to 3.

None of the single-administration groups were found to have (p>0.05) a significant life-prolonging effect as compared with the group not administered with any agents. On the other hand, the test compound and fluconazole, the test compound and amphotericin B and the test compound and micafungin combined-administration groups were found to have (p≤0.0001) a significant life-prolonging effect as compared with the group not administered with any agents.

In the *Candida albicans* mouse systemic infection model, the combined administration of the test compound and fluconazole, the test compound and amphotericin B and the test compound and micafungin was found to exhibit excellent treatment effects.

Test Example 4

In Vivo Test (*Aspergillus*)

In vivo activity was evaluated employing a mouse systemic infection model using *Aspergillus fumigatus*.

As for the inoculum, mice (four-week old (at infection) male ICR mice, 10 mice per group) were intraperitoneally administered with cyclophosphamide 4 days prior to infection (200 mg/kg) and the day after infection (100 mg/kg). A conidium suspension of *Aspergillus fumigatus* TIMM0063 was diluted with sterile physiological saline solution containing 0.05% Tween 80 (manufactured by Difco Laboratories) to prepare an inoculum. The mice were intravenously inoculated in their tails with 0.2 mL of the inoculum to induce infection (approximately $4 \times 10^4$ CFU/mouse).

The test compound was dissolved in a small amount of 0.1 mol/L hydrochloric acid, and the resultant solution was diluted with sterile physiological saline solution.

Voriconazole was dissolved in 50 mg/mL aqueous sulfobutyl ether β-cyclodextrin sodium (SIDIX) solution.

Flucytosine was suspended in 0.5% methyl cellulose solution.

The test compound (0.1 mg/kg) and voriconazole (5 mg/kg) were subcutaneously administered and flucytosine (50 mg/kg) was orally administered 2 hours after infection and then once a day for 6 days for a total of 7 times. The test was carried out for the case where each of the agents was administered singly and in combination by administering each of the agents immediately after the test compound had been administered. Efficacy in the susceptibility test was evaluated by the survival rate 15 days after infection.

The results of the combination of the test compound and voriconazole against *Aspergillus fumigatus* are shown in Table 4. The results of the combination of the test compound and flucytosine against *Aspergillus fumigatus* are shown in Table 5.

TABLE 4

| Composition | Test Compound | VLCZ | Test Compound VLCZ | Non-administered group |
|---|---|---|---|---|
| Survival rate (%) | 10 | 10 | 50 | 0 |

TABLE 5

| Composition | Test Compound | 5-FC | Test Compound 5-FC | Non-administered group |
|---|---|---|---|---|
| Survival rate (%) | 10 | 10 | 50 | 0 |

In the *Aspergillus fumigatus* mouse systemic infection model, the combined administration of the test compound and voriconazole and the test compound and flucytosine exhibited excellent treatment effects.

Test Example 5

In Vivo Test (*Cryptococcus*)

In vivo activity was evaluated employing a mouse systemic infection model using *Cryptococcus neoformans*.

Mice (four-week old (at infection) male ICR mice, 10 mice per group) were intraperitoneally administered with cyclophosphamide 4 days prior to infection (200 mg/kg) and the day after infection (100 mg/kg). An inoculum was prepared by suspending in sterile physiological saline solution *Cryptococcus neoformans* ATCC90112 on a SDA flat plate that had been cultured for one night at 35° C., counting the number of cells using a biological microscope, and then diluting with sterile physiological saline solution. The mice were intravenously inoculated in their tails with 0.2 mL of the inoculum to induce infection (approximately $8\times10^4$ CFU/mouse).

The test compound was dissolved in a small amount of 0.1 mol/L hydrochloric acid, and the resultant solution was diluted with sterile physiological saline solution.

Fluconazole was prepared using sterile physiological saline solution.

Amphotericin B was dissolved in a 5% aqueous glucose solution.

The test compound (0.125 mg/kg), fluconazole (5 mg/kg) and amphotericin B (0.25 mg/kg) were subcutaneously administered 2 hours after infection and then once a day for 6 days a total of 7 times. The test was carried out for the case where the each of the agents was administered singly and in combination by administering each of the agents immediately after the test compound had been administered. Efficacy in the susceptibility test was evaluated by the survival rate 22 days after infection.

The results of the combination of the test compound with fluconazole against *Cryptococcus neoformans* are shown in Table 6. The results of the combination of the test compound with amphotericin B against *Cryptococcus neoformans* are shown in Table 7.

TABLE 6

| Composition | Test Compound | FLCZ | Test Compound FLCZ | Non-administered group |
|---|---|---|---|---|
| Survival rate (%) | 20 | 10 | 80 | 0 |

TABLE 7

| Composition | Test Compound | AMPH-B | Test Compound AMPH-B | Non-administered group |
|---|---|---|---|---|
| Survival rate (%) | 0 | 20 | 70 | 0 |

In the *Cryptococcus neoformans* mouse systemic infection model, the combined administration of the test compound and fluconazole and that of the test compound and amphotericin B exhibited excellent treatment effects.

It is clear from the above results that the combination of the arylamidine derivative or the salt thereof represented by general formula [1] with various antifungal agents or the like exhibits synergistic antifungal activity and treatment effects, and is effective in the treatment of fungal infections caused by fungal pathogens.

Next, the arylamidine derivative or the salt thereof represented by general formula [1] used in the present invention will be described with reference to Production Examples and Drug Formulation Examples.

The mixing ratio in the eluent is by capacity ratio. Unless otherwise noted, the carrier for the silica gel column chromatography is B.W. Silica Gel, BW-127ZH, Fuji Silysia Chemical Ltd.

The respective abbreviations have the following meaning.

Ac: acetyl; Boc: tert-butoxycarbonyl; Et: ethyl; DMSO-$d_6$: deuterated Dimethylsulfoxide.

Production Example 1

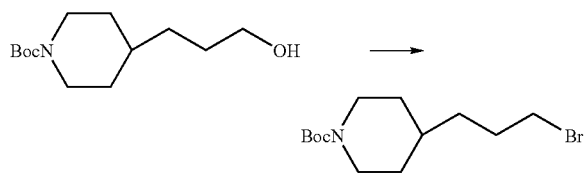

To a tetrahydrofuran (110 mL) solution of 10.7 g of tert-butyl 4-(3-hydroxypropyl)-1-piperidinecarboxylate was added 19.0 g of carbon tetrabromide under cooling with water, to which 15.0 g of triphenylphosphine was then added over a period of 13 minutes. This mixture was stirred at room temperature for 2 hours and 30 minutes and allowed to stand for 13 hours. To the reaction mixture were added water, ethyl acetate, and a saturated sodium chloride aqueous solution. The organic layer was separated, washed with a saturated sodium chloride aqueous solution, and dried with anhydrous magnesium sulfate, followed by distilling off the solvent under reduced pressure. The resultant residue was purified using silica gel column chromatography (eluent; hexane:ethyl acetate=3:1) to provide 13.2 g of tert-butyl 4-(3-bromopropyl)-1-piperidinecarboxylate as colorless oily form.

$^1$H-NMR (CDCl$_3$) δ value: 1.00-1.20 (2H, m), 1.20-1.50 (3H, m), 1.45 (9H, s), 1.60-1.70 (2H, m), 1.80-1.95 (2H, m), 2.60-2.75 (2H, m), 3.40 (2H, t, J=6.8 Hz), 3.90-4.25 (2H, m).

Production Example 2

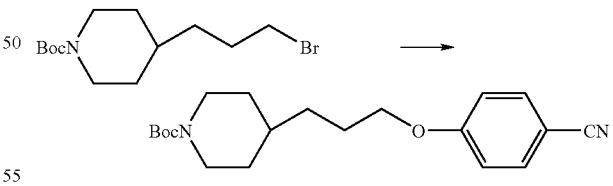

To a dimethylsulfoxide (130 mL) solution of 13.2 g of tert-butyl 4-(3-bromopropyl)-1-piperidinecarboxylate were added 5.13 g of 4-cyanophenol and 11.9 g of potassium carbonate at room temperature, which was then stirred at the same temperature for 26 hours. The reaction mixture was added to a mixture of toluene and water. The organic layer was separated, washed with a saturated sodium chloride aqueous solution, and dried with anhydrous magnesium sulfate, followed by distilling off the solvent under reduced pressure to provide 14.5 g of tert-butyl 4-[3-(4-cyanophenoxy)propyl]-1-piperidinecarboxylate as white solid form.

$^1$H-NMR (CDCl$_3$) δ value: 1.05-1.20 (2H, m), 1.40-1.50 (3H, m), 1.46 (9H, s), 1.65-1.75 (2H, m), 1.75-1.90 (2H, m), 2.60-2.80 (2H, m), 3.99 (2H, t, J=6.3 Hz), 4.00-4.20 (2H, m), 6.93 (2H, d, J=8.7 Hz), 7.58 (2H, d, J=8.7 Hz).

Production Example 3

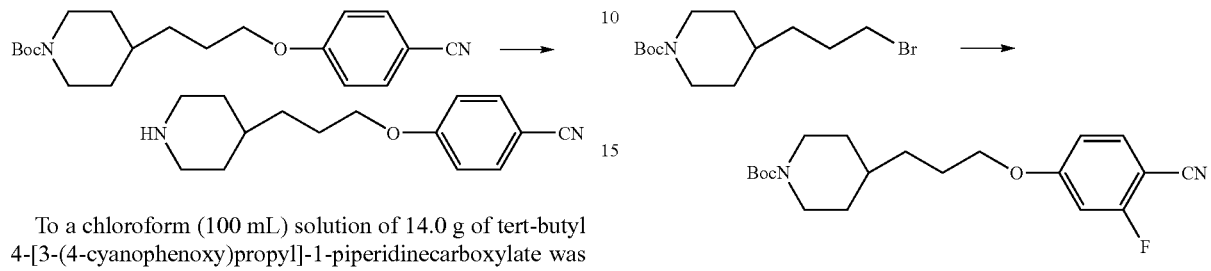

To a chloroform (100 mL) solution of 14.0 g of tert-butyl 4-[3-(4-cyanophenoxy)propyl]-1-piperidinecarboxylate was dropwise added 40 mL of trifluoroacetic acid under cooling with water over a period of 10 minutes. This mixture was stirred at the same temperature for 20 minutes, and then stirred at room temperature for 35 minutes. After distilling off the solvent under reduced pressure, chloroform and water were added. A sodium hydroxide aqueous solution was added thereto for adjustment to pH 13.0. The organic layer was separated, and the aqueous layer was extracted with chloroform. The organic layer and the extract were combined, which was then washed with a sodium hydroxide aqueous solution and dried with potassium carbonate, followed by distilling off the solvent under reduced pressure to provide 10.3 g of 4-[3-(4-piperidinyl)propoxy]benzonitrile as pale yellow solid form.

$^1$H-NMR (CDCl$_3$) δ value: 1.05-1.20 (2H, m), 1.35-1.45 (3H, m), 1.65-1.90 (4H, m), 2.50-2.65 (2H, m), 3.00-3.15 (2H, m), 3.99 (2H, t, J=6.6 Hz), 4.78 (1H, s), 6.93 (2H, d, J=9.0 Hz), 7.58 (2H, d, J=9.0 Hz).

Production Example 4

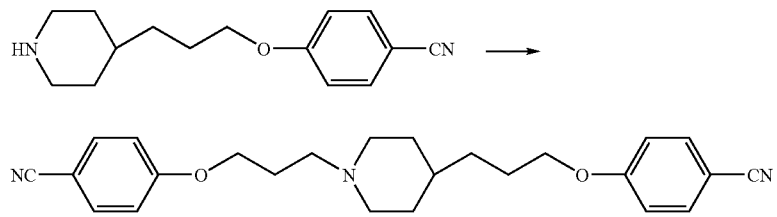

To an N,N-dimethylformamide (150 mL) solution of 10.2 g of 4-[3-(4-piperidinyl)propoxy]benzonitrile were sequentially added 11.2 g of potassium carbonate and 9.72 g of 4-(3-bromopropoxy)benzonitrile at room temperature, which was then stirred at the same temperature for 18 hours. Toluene and water were added to the reaction mixture. The precipitate was collected by filtration to provide 13.7 g of 4-(3-{4-[3-(4-cyanophenoxy)propyl]-1-piperidinyl}propoxy)benzonitrile as white solid form.

$^1$H-NMR (CDCl$_3$) δ value: 1.20-1.45 (5H, m), 1.65-2.05 (8H, m), 2.40-2.55 (2H, m), 2.85-3.00 (2H, m), 3.99 (2H, t, J=6.5 Hz), 4.06 (2H, t, J=6.3 Hz), 6.93 (2H, d, J=8.8 Hz), 6.94 (2H, d, J=8.8 Hz), 7.57 (2H, d, J=8.8 Hz), 7.57 (2H, d, J=8.8 Hz).

Production Example 5

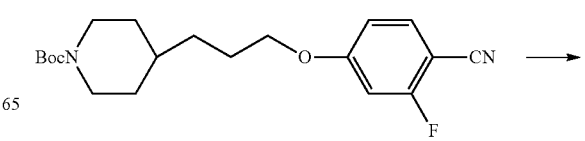

A 2-butanone (7.6 mL) solution of 1.12 g of tert-butyl 4-(3-bromopropyl)-1-piperidinecarboxylate was added to a 2-butanone (7.0 mL) mixture of 0.50 g of 2-fluoro-4-hydroxybenzonitrile and 0.56 g of potassium carbonate, which was then heated to reflux for 6 hours and 30 minutes. After cooling down to room temperature, the reaction mixture was added to a mixture of ethyl acetate and water. The organic layer was separated, washed with water, and dried with anhydrous magnesium sulfate, followed by distilling off the solvent under reduced pressure. The resultant residue was purified using silica gel column chromatography (eluent; hexane: ethyl acetate=4:1) to provide 0.72 g of tert-butyl 4-[3-(4-cyano-3-fluorophenoxy)propyl]-1-piperidinecarboxylate as colorless oily form.

$^1$H-NMR (CDCl$_3$) δ value: 1.05-1.20 (2H, m), 1.35-1.45 (3H, m), 1.46 (9H, s), 1.65-1.75 (2H, m), 1.75-1.90 (2H, m), 2.60-2.75 (2H, m), 3.99 (2H, t, J=6.3 Hz), 4.00-4.20 (2H, m), 6.65-6.80 (2H, m), 7.45-7.54 (1H, m).

Production Example 6

-continued

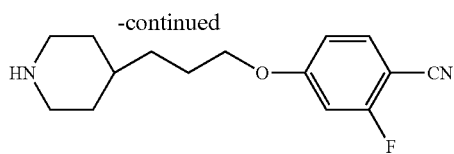

To a methylene chloride (5.5 mL) solution of 0.66 g of tert-butyl 4-[3-(4-cyano-3-fluorophenoxy) propyl]-1-piperidinecarboxylate was dropwise added 1.8 mL of trifluoroacetic acid under cooling with ice over a period of 2 minutes, which was then stirred at room temperature for 6 hours. The solvent was distilled off under reduced pressure, and chloroform and a 1.0 mol/L sodium hydroxide aqueous solution were added to the resultant residue. The organic layer was separated and dried with anhydrous magnesium sulfate, followed by distilling off the solvent under reduced pressure.

of 4-(3-bromopropoxy)benzonitrile at room temperature, which was then stirred at the same temperature for 13 hours. Ethyl acetate, water, and toluene were added to the reaction mixture. The organic layer was separated and dried with anhydrous sodium sulfate, followed by distilling off the solvent under reduced pressure. The resultant residue was purified using silica gel column chromatography (eluent; chloroform:methanol=4:1) to provide 68 mg of 4-(3-{1-[3-(4-cyanophenoxy)propyl]-4-piperidinyl}propoxy)-2-fluorobenzonitrile as white solid form.

$^1$H-NMR (CDCl$_3$) δ value: 1.20-1.45 (5H, m), 1.65-2.05 (8H, m), 2.40-2.55 (2H, m), 2.85-3.00 (2H, m), 3.98 (2H, t, J=6.5 Hz), 4.06 (2H, t, J=6.3 Hz), 6.69 (1H, dd, J=11.0, 2.4 Hz), 6.74 (1H, dd, J=8.8, 2.4 Hz), 6.94 (2H, d, J=8.7 Hz), 7.45-7.55 (1H, m), 7.57 (2H, d, J=8.7 Hz)

Production Example 8

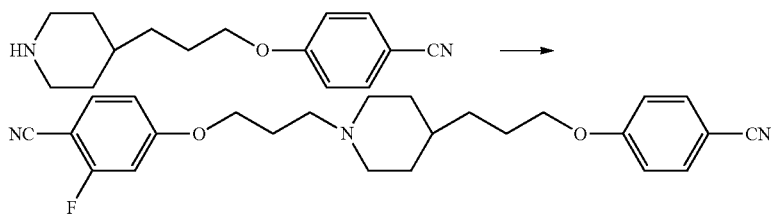

The resultant residue was purified using silica gel column chromatography (eluent; chloroform:methanol=4:1) to provide 0.28 g of 2-fluoro-4-[3-(4-piperidinyl)propoxy] benzonitrile as pale yellow oily form.

$^1$H-NMR (CDCl$_3$) δ value: 1.05-1.20 (2H, m), 1.30-1.45 (3H, m), 1.50-1.75 (2H, m), 1.75-1.90 (2H, m), 2.50-2.65 (2H, m), 3.00-3.15 (2H, m), 3.98 (2H, t, J=6.5 Hz), 6.69 (1H, dd, J=11.0, 2.3 Hz), 6.75 (1H, dd, J=8.5, 2.3 Hz), 7.50 (1H, dd, J=8.5, 8.5 Hz).

Production Example 7

As described in Production Example 7, 0.12 g of 4-[3-(4-piperidinyl)propoxy]benzonitrile and 0.15 g of 4-(3-bromopropoxy)-2-fluorobenzonitrile were used to provide 0.10 g of 4-(3-{4-[3-(4-cyanophenoxy)propyl]-1-piperidinyl}propoxy)-2-fluorobenzonitrile as white solid form.

$^1$H-NMR (CDCl$_3$) δ value: 1.20-1.35 (3H, m), 1.35-1.45 (2H, m), 1.60-2.05 (8H, m), 2.40-2.50 (2H, m), 2.85-3.00

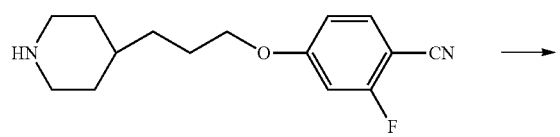

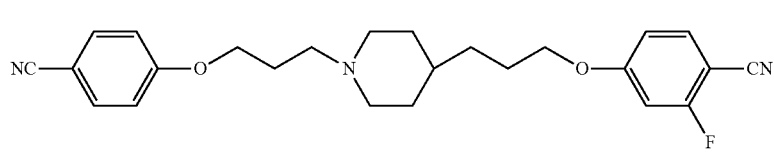

To an N,N-dimethylformamide solution (2.0 mL) of 0.10 g of 2-fluoro-4-[3-(4-piperidinyl)propoxy]benzonitrile were sequentially added 0.10 g of potassium carbonate and 0.13 g (2H, m), 3.99 (2H, t, J=6.5 Hz), 4.06 (2H, t, J=6.3 Hz), 6.70-6.80 (2H, m), 6.93 (2H, d, J=9.0 Hz), 7.45-7.55 (1H, m), 7.57 (2H, d, J=9.0 Hz).

Production Example 9

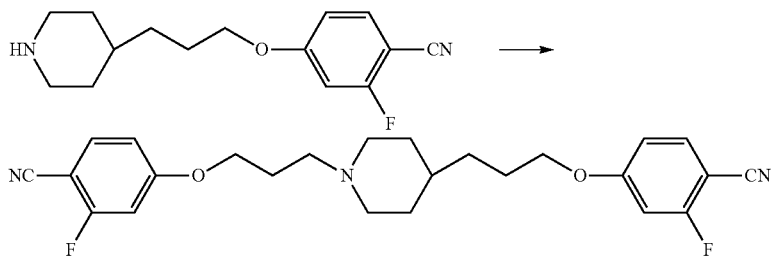

To a dimethylsulfoxide (4.0 mL) solution of 0.26 g of 2-fluoro-4-[3-(4-piperidinyl)propoxy]benzonitrile and 0.21 g of 4-(3-chloropropoxy)-2-fluorobenzonitrile was added 0.88 mL of N-ethyldiisopropylamine, which was then stirred at 80 to 90° C. for 8 hours and 15 minutes. The reaction mixture was cooled down to room temperature, to which water was then added, followed by extraction with ethyl acetate. The extract was washed twice with water and dried with anhydrous magnesium sulfate, followed by distilling off the solvent under reduced pressure. The resultant residue was purified using silica gel column chromatography (eluent; chloroform:methanol=10:1) to provide 0.25 g of 4-(3-{1-[3-(4-cyano-3-fluorophenoxy) propyl]-4-piperidinyl}propoxy)-2-fluorobenzonitrile as brown solid form.

$^1$H-NMR (CDCl$_3$) δ value: 1.20-1.45 (5H, m), 1.65-2.05 (8H, m), 2.40-2.50 (2H, m), 2.85-3.00 (2H, m), 3.98 (2H, t, J=6.5 Hz), 4.06 (2H, t, J=6.3 Hz), 6.65-6.80 (4H, m), 7.45-7.55 (2H, m).

Production Example 10

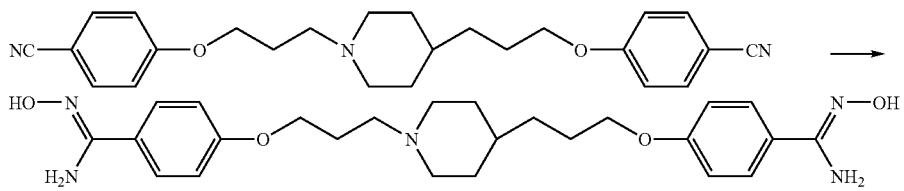

To a dimethylsulfoxide (126 mL) suspension of 12.6 g of 4-(3-{4-[3-(4-cyanophenoxy)propyl]-1-piperidinyl}propoxy)benzonitrile was added 19.1 mL of a 50% hydroxylamine aqueous solution, which was then stirred at 50° C. for 19 hours. The mixture was cooled down to room temperature, to which 260 mL of water was added dropwise over a period of 50 minutes, followed by stirring at room temperature for 30 minutes and then under cooling with water for 2 hours. The precipitate was collected by filtration to provide 15.0 g of 4-{3-[4-(3-{4-[amino(hydroxyimino)methyl]phenoxy}propyl)-1-piperidinyl]propoxy}-N'-hydroxybenzamidine as white solid form.

$^1$H-NMR (DMSO-d$_6$) δ value: 1.05-1.40 (5H, m), 1.60-1.80 (4H, m), 1.80-1.90 (4H, m), 2.35-2.45 (2H, m), 2.80-2.90 (2H, m), 3.96 (2H, t, J=6.5 Hz), 4.01 (2H, t, J=6.5 Hz), 5.65-5.75 (4H, m), 6.85-6.95 (4H, m), 7.55-7.65 (4H, m), 9.43 (1H, s), 9.43 (1H, s).

Production Example 11

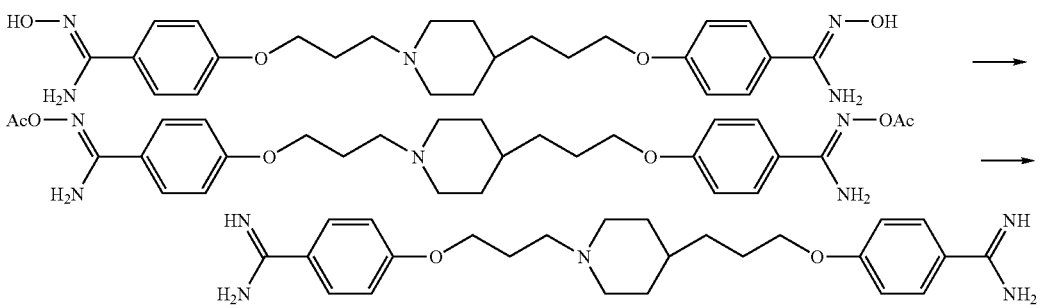

To an acetic acid (150 mL) suspension of 14.9 g of 4-{3-[4-(3-{4-[amino(hydroxyimino)methyl]phenoxy}propyl)-1-piperidinyl]propoxy}-N'-hydroxybenzamidine was added 5.97 mL of acetic anhydride at room temperature, which was then stirred at room temperature for 1 hour and 20 minutes. To this mixture was added 1.50 g of 5% palladium-carbon, which was then stirred under hydrogen atmosphere for 4 hours and 40 minutes. Insoluble matter was filtered off, and 55 mL of 6.0 mol/L hydrochloric acid was then added. The solvent was distilled off under reduced pressure, and ethanol was added to the resultant residue. The solid matter was collected by filtration to provide 14.0 g of 4-{3-[4-(3-{4-[amino(imino)methyl]phenoxy}propyl)-1-piperidinyl]propoxy}benzamidine as white solid form.

$^1$H-NMR (DMSO-$d_6$) δ value: 1.30-1.45 (2H, m), 1.45-1.70 (3H, m), 1.70-1.90 (4H, m), 2.15-2.30 (2H, m), 2.80-3.00 (2H, m), 3.10-3.20 (2H, m), 3.45-3.55 (2H, m), 4.10 (2H, t, J=6.2 Hz), 4.19 (2H, t, J=6.1 Hz), 7.15 (2H, d, J=8.4 Hz), 7.16 (2H, d, J=8.4 Hz), 7.84 (2H, d, J=8.4 Hz), 7.86 (2H, d, J=8.4 Hz), 8.90-9.00 (4H, m), 9.15-9.30 (4H, m), 10.60-10.80 (1H, broad).

Production Example 12 resultant residue was dissolved in 20 mL of ethanol. Thereto was added 1.54 g of ammonium acetate, which was then heated to reflux for 3 hours and 45 minutes. The reaction mixture was cooled down to room temperature, to which water was added, followed by distilling off ethanol under reduced pressure. Chloroform was added to the resultant residue, to which a 5.0 mol/L sodium hydroxide aqueous solution was then added to adjust the pH to 12.5. The precipitate was collected by filtration to provide 1.13 g of 4-{3-[4-(3-{4-[amino(imino)methyl]phenoxy}propyl)-1-piperidinyl]propoxy}benzamidine as white solid form.

$^1$H-NMR (DMSO-$d_6$) δ value: 1.00-1.40 (5H, m), 1.60-1.80 (4H, m), 1.80-1.95 (4H, m), 2.35-2.45 (2H, m), 2.80-2.90 (2H, m), 3.98 (2H, t, J=6.5 Hz), 4.03 (2H, t, J=6.3 Hz), 6.30-7.20 (4H, broad), 6.85-7.00 (4H, m), 7.65-7.80 (4H, m).

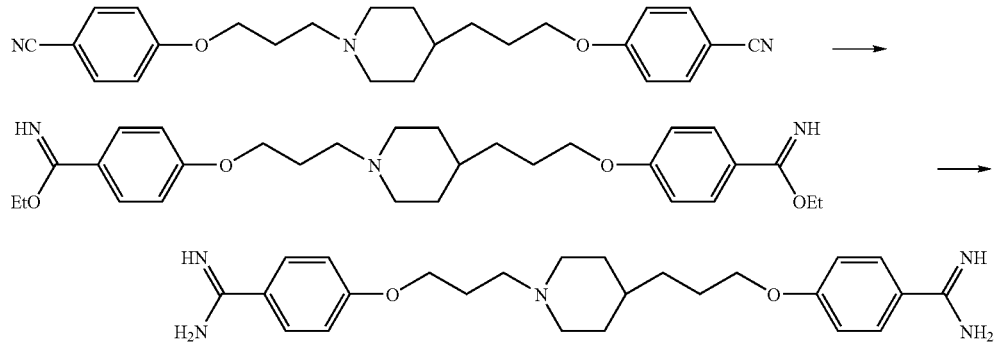

Hydrogen chloride was introduced into an ethanol (20 mL) suspension of 1.15 g of 4-(3-{4-[3-(4-cyanophenoxy)propyl]-1-piperidinyl}propoxy)benzonitrile under cooling with ice, which was then stirred at room temperature for 24 hours. The solvent was distilled off under reduced pressure, and the Production Example 13

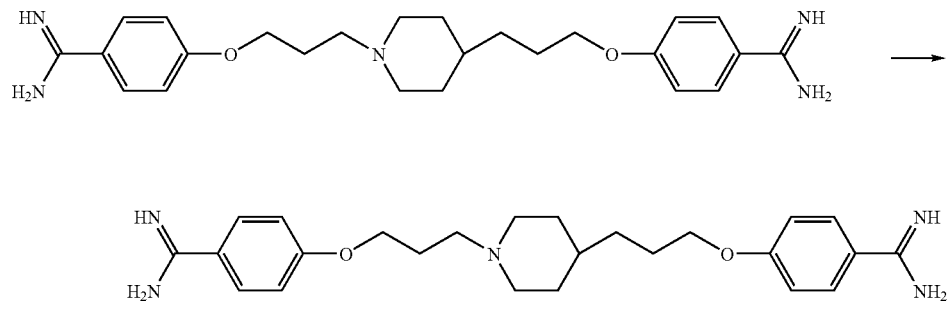

To an ethanol (10 mL) suspension of 0.50 g of 4-{3-[4-(3-{4-[amino(imino)methyl]phenoxy}propyl)-1-piperidinyl]propoxy}benzamidine was added 1.77 mL of a 2.6 mol/mL hydrogen chloride/ethanol solution at room temperature, which was then stirred at room temperature for 4 hours and 15 minutes. The precipitate was collected by filtration to provide 0.49 g of 4-{3-[4-(3-{4-[amino(imino)methyl]phenoxy}propyl)-1-piperidinyl]propoxy}benzamidine hydrochloride as colorless solid form.

¹H-NMR spectral data in DMSO-d₆ agreed with the values of Production Example 11.

Production Example 14

To an acetic acid (2.0 mL) suspension of 56 mg of 4-{3-[1-(3-{4-[amino(hydroxyimino)methyl]phenoxy}propyl)-4-piperidinyl]propoxy}-2-fluoro-N'-hydroxybenzamidine was added 0.043 mL of acetic anhydride at room temperature, which was then stirred at the same temperature for one hour. To this mixture was added 5.0 mg of 5% palladium-carbon, which was then stirred under hydrogen atmosphere for 2 hours. Insoluble matter was filtered off, and the solvent was distilled off under reduced pressure. Thereto were added 6.0 mol/L hydrochloric acid and water, followed by distilling off the solvent under reduced pressure. The resultant residue was

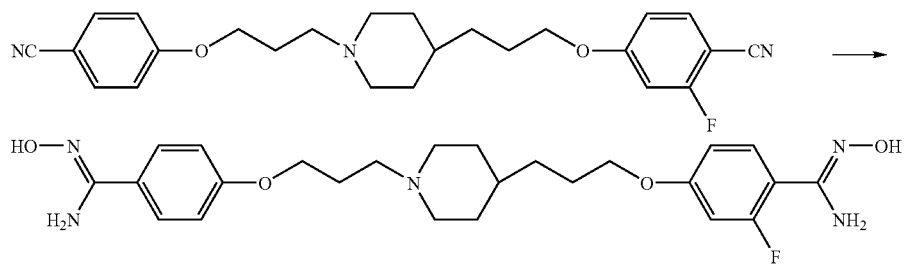

To a dioxane (3.0 mL) suspension of 67 mg of 4-(3-{1-[3-(4-cyanophenoxy)propyl]-4-piperidinyl}propoxy)-2-fluorobenzonitrile was added 1.0 mL of a 50% hydroxylamine aqueous solution, which was then heated to reflux for 2 hours. The mixture was cooled down to room temperature, to which 10 mL of water was then added dropwise, followed by stirring under cooling with ice for 30 minutes. The precipitate was collected by filtration to provide 63 mg of 4-{3-[1-(3-{4-[amino (hydroxyimino)methyl]phenoxy}propyl)-4-piperidinyl]propoxy}-2-fluoro-N'-hydroxybenzamidine as pale yellow solid form.

¹H-NMR (DMSO-d₆) δ value: 1.00-1.40 (5H, m), 1.60-1.80 (4H, m), 1.80-1.95 (4H, m), 2.35-2.45 (2H, m), 2.80-2.90 (2H, m), 3.98 (2H, t, J=6.4 Hz), 4.00 (2H, t, J=6.0 Hz), 5.60-5.80 (4H, m), 6.70-6.85 (2H, m), 6.90 (2H, d, J=8.8 Hz), 7.35-7.45 (1H, m), 7.58 (2H, d, J=8.8 Hz), 9.43 (1H, s), 9.50 (1H, s).

Production Example 15 purified using silica gel column chromatography (silica gel: ODS-AM120-S50 from YMC, eluent; water). The resultant residue was dissolved in 5.0 mL of water, to which a 5.0 mol/L sodium hydroxide aqueous solution was then added to adjust the pH to 12.2. The solution was stirred under cooling with ice for 20 minutes, and the precipitate was collected by filtration to provide 43 mg of 4-{3-[1-(3-{4-[amino(imino)methyl]phenoxy}propyl)-4-piperidinyl]propoxy}-2-fluorobenzamidine as white solid form.

¹H-NMR (DMSO-d₆) δ value: 1.05-1.40 (5H, m), 1.60-2.05 (8H, m), 2.30-2.45 (2H, m), 2.80-2.90 (2H, m), 3.98 (2H, t, J=6.5 Hz), 4.02 (2H, t, J=6.3 Hz), 6.20-6.70 (4H, broad), 6.75-6.85 (2H, m), 6.92 (2H, d, J=8.4 Hz), 7.45-7.55 (1H, m), 7.71 (2H, d, J=8.4 Hz).

Production Example 16

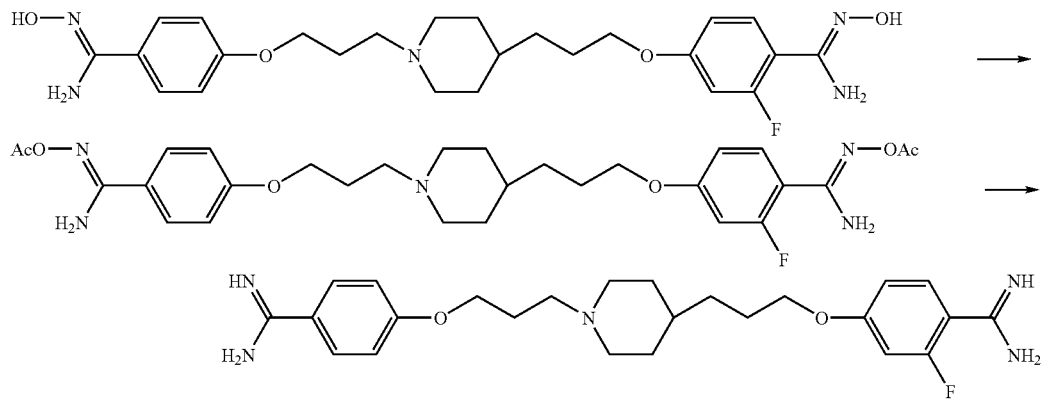

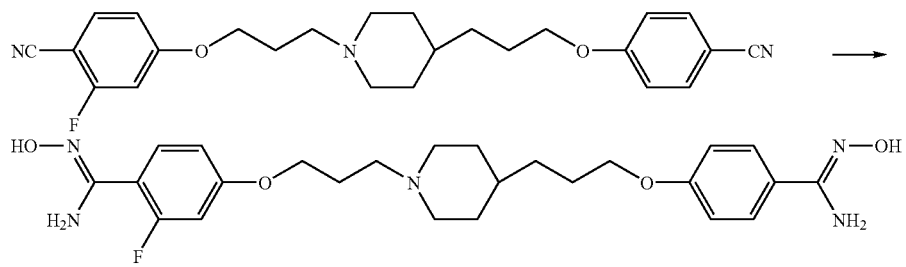

As described in Production Example 14, 0.10 g of 4-3-{4-[3-(4-cyanophenoxy)propyl]-1-piperidinyl}propoxy)-2-fluorobenzonitrile was used to provide 0.11 g of 4-{3-[4-(3-{4-[amino(hydroxyimino)methyl]phenoxy}propyl)-1-piperidinyl]propoxy}-2-fluoro-N'-hydroxybenzamidine as white solid form.

$^1$H-NMR (DMSO-$d_6$) δ value: 1.00-1.40 (5H, m), 1.60-1.75 (4H, m), 1.75-1.90 (4H, m), 2.30-2.40 (2H, m), 2.80-2.90 (2H, m), 3.96 (2H, t, J=6.5 Hz), 4.03 (2H, t, J=6.3 Hz), 5.65-5.80 (4H, m), 6.75-6.90 (2H, m), 6.90 (2H, d, J=8.9 Hz), 7.35-7.45 (1H, m), 7.58 (2H, d, J=8.9 Hz), 9.43 (1H, s), 9.50 (1H, s).

As described in Production Example 15, 90 mg of 4-{3-[4-(3-{4-[amino(hydroxyimino)methyl]phenoxy}propyl)-1-piperidinyl]propoxy}-2-fluoro-N'-hydroxybenzamidine was used to provide 34 mg of 4-{3-[4-(3-{4-[amino(imino)methyl]phenoxy}propyl)-1-piperidinyl]propoxy}-2-fluorobenzamidine as white solid form.

$^1$H-NMR (DMSO-$d_6$) δ value: 1.05-1.40 (5H, m), 1.60-1.90 (8H, m), 2.30-2.45 (2H, m), 2.80-2.90 (2H, m), 3.98 (2H, t, J=6.5 Hz), 4.03 (2H, t, J=6.0 Hz), 6.30-6.75 (4H, broad), 6.75-6.85 (2H, m), 6.93 (2H, d, J=8.7 Hz), 7.45-7.55 (1H, m), 7.71 (2H, d, J=8.7 Hz).

Production Example 17

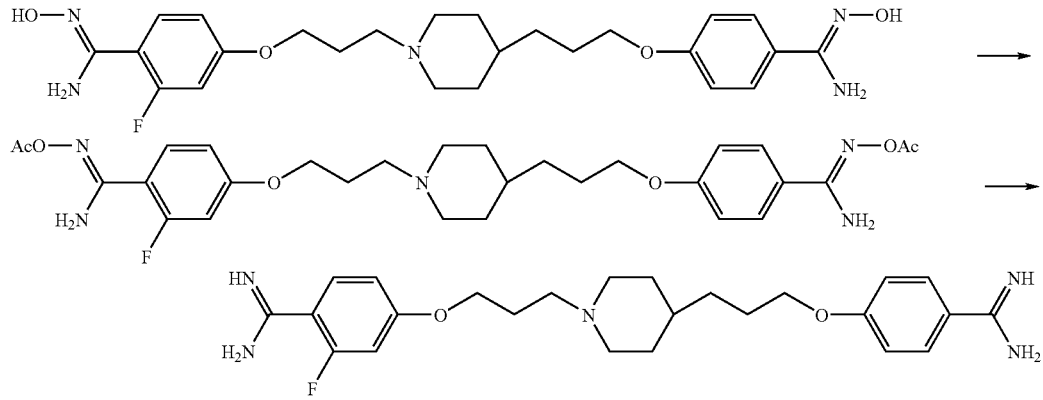

Production Example 18

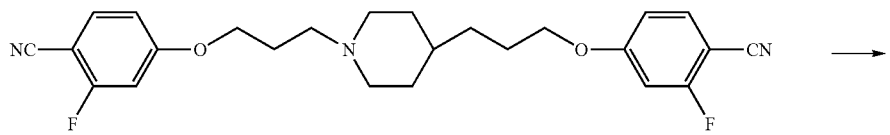

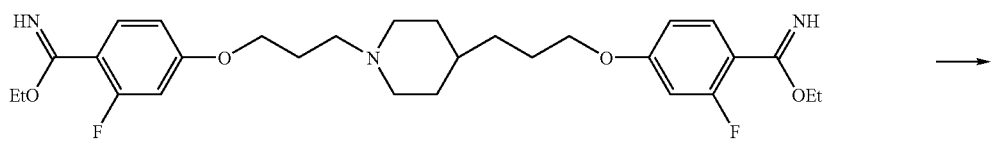

-continued

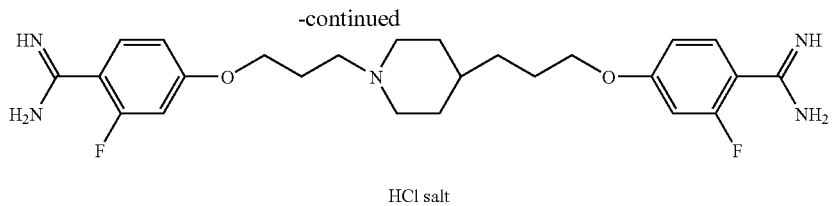

HCl salt

Hydrogen chloride was introduced into an ethanol (10 mL) suspension of 0.10 g of 4-(3-{1-[3-(4-cyano-3-fluorophenoxy)propyl]-4-piperidinyl}propoxy)-2-fluorobenzonitrile under cooling with ice, which was then stirred at the same temperature for 1 hour and 10 minutes and at room temperature for 17 hours. The solvent was distilled off under reduced pressure, and the resultant residue was suspended in 5.0 mL of ethanol, to which 44 mg of ammonium acetate was then added, followed by heating to reflux for 5 hours and 30 minutes. The solvent was distilled off under reduced pressure, and the resultant residue was dissolved in 8.0 mL of 1.0 mol/L hydrochloric acid, followed by distilling off the solvent under reduced pressure. The resultant residue was purified using silica gel column chromatography (silica gel: ODS-AM120-S50 from YMC, eluent; water) to provide 46 mg of 4-{3-[1-(3-{4-[amino(imino)methyl]-3-fluorophenoxy}propyl)-4-piperidinyl]propoxy}-2-fluorobenzamidine hydrochloride as white solid form.

$^1$H-NMR (DMSO-$d_6$) δ value: 1.30-1.45 (2H, m), 1.50-1.70 (3H, m), 1.70-1.90 (4H, m), 2.20-2.30 (2H, m), 2.80-2.95 (2H, m), 3.10-3.20 (2H, m), 3.40-3.55 (2H, m), 4.10 (2H, t, J=6.0 Hz), 4.20 (2H, t, J=5.7 Hz), 6.95-7.05 (2H, m), 7.05-7.15 (2H, m), 7.60-7.75 (2H, m), 9.20-9.50 (8H, m), 10.95-11.10 (1H, broad).

Drug Formulation Example 1

To water for injection were dissolved 1.25 g of the compound obtained in Production Example 11 and 5.0 g of D-mannitol to provide a total amount of 100 mL. The solution was filtered through a 0.22-µm membrane filter, and 10 mL of the resultant drug solution was packed in an ampule and sealed, followed by steam sterilization to provide an injection agent.

INDUSTRIAL APPLICABILITY

A pharmaceutical composition having the antifungal activity according to the present invention comprising an arylamidine derivative or a salt thereof, and one or more agents selected from azole antifungal agents, polyene antifungal agents, candin antifungal agents, fluoropyrimidine antifungal agents and immunosuppressants, has a strong antifungal activity and is useful in treating fungal infections caused by fungal pathogens. Further, the treatment method according to the present invention is useful as an excellent treatment method of fungal infections.

Figure 1:
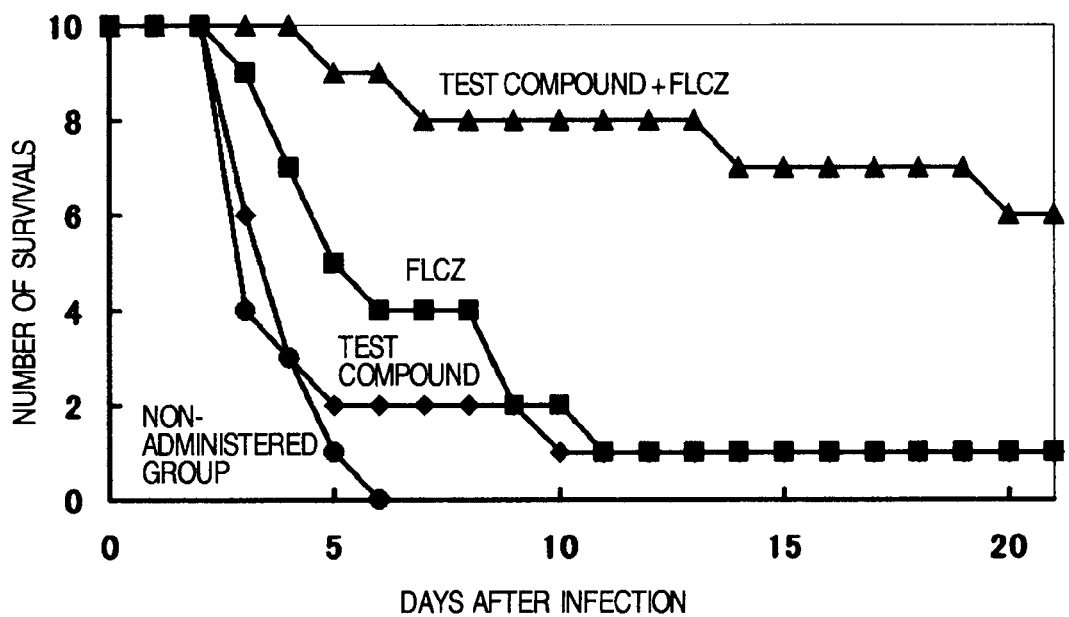
FIG. 1 is a survival curve for the results of using FLCZ together with the test compound (Test Example 2). The closed circles denote the results for the group not administered with any agents; the closed squares denote the results for the group administered with 0.25 mg/kg of FLCZ; the closed diamonds denote the results for the group administered with 0.0313 mg/kg of the test compound; and the closed triangles denote the results for the group administered with 0.0313 mg/kg of the test compound and 0.25 mg/kg of FLCZ.
Figure 2:
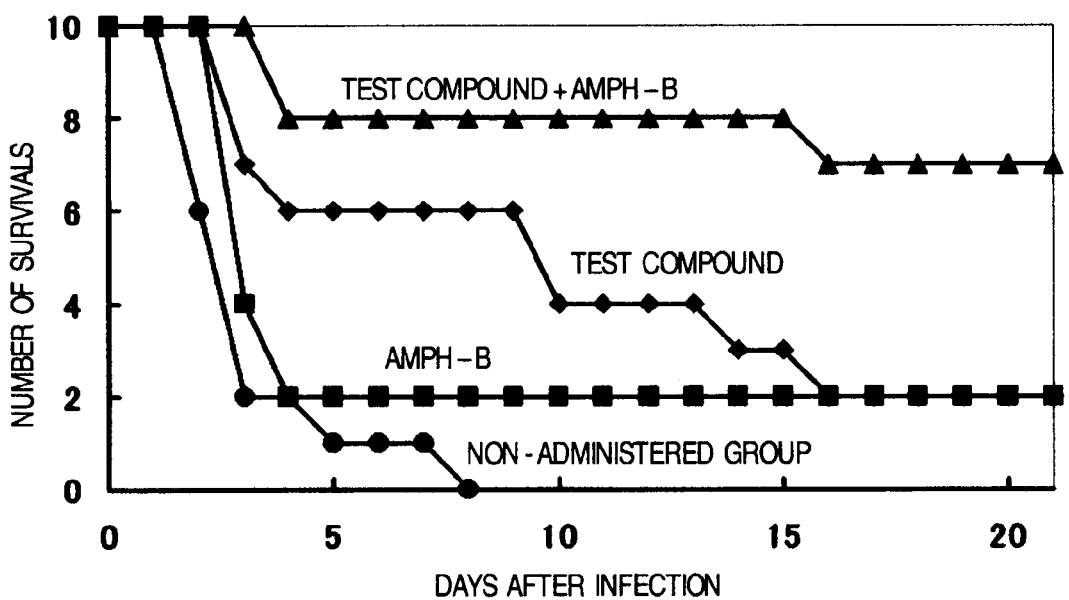
FIG. 2 is a survival curve for the results of using AMPH-B together with the test compound (Test Example 2). The closed circles denote the results for the group not administered with any agents; the closed squares denote the results for the group administered with 0.1 mg/kg of AMPH-B; the closed diamonds denote the results for the group administered with 0.0313 mg/kg of the test compound; and the closed triangles denote the results for the group administered with 0.0313 mg/kg of the test compound and 0.1 mg/kg of AMPH-B.
Figure 3:
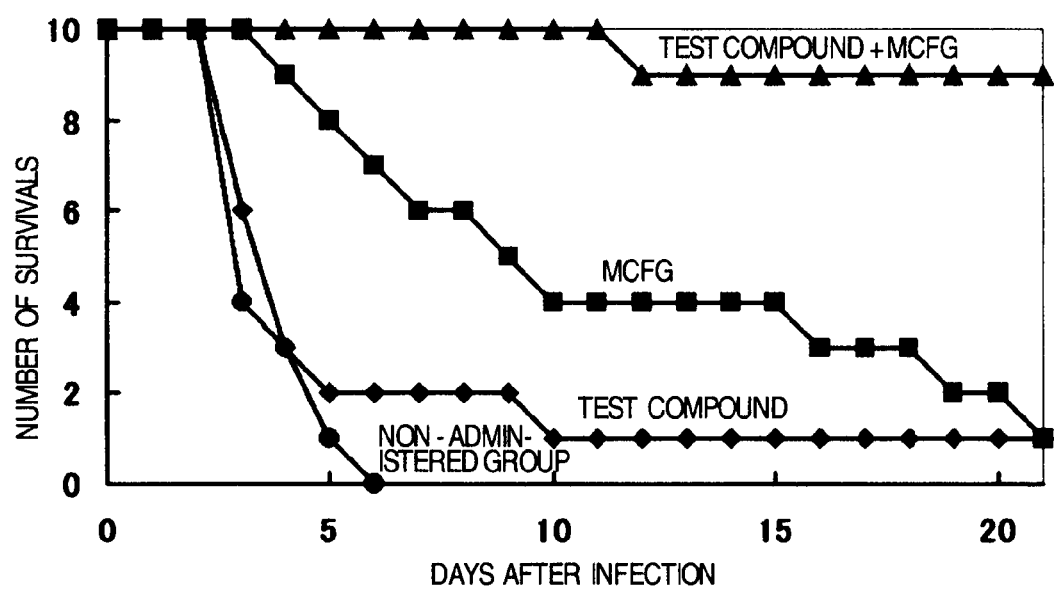
FIG. 3 is a survival curve for the results of using MCFG together with the test compound (Test Example 2). The closed circles denote the results for the group not administered with any agents; the closed squares denote the results for the group administered with 0.25 mg/kg of MCFG; the closed diamonds denote the results for the group administered with 0.0313 mg/kg of the test compound; and the closed triangles denote the results for the group administered with 0.0313 mg/kg of the test compound and 0.25 mg/kg of MCFG.

The invention claimed is:

1. A pharmaceutical composition for treating fungal infections, comprising:
   (A) 4-{3-[4-(3-{4-[amino(imino)methyl]phenoxy}propyl)-1-piperidinyl]propoxy}benzamidine and
   (B) one or more agents selected from the group consisting of fluconazole, voriconazole, itraconazole, ketoconazole, amphotericin B, micafungin, flucytosine, and tacrolimus,
   wherein the fungal infection is caused by a fungal pathogen selected from *Candida albicans, Cryptococcus neoformans, Aspergillus fumigatus*, and *Malassezia furfur*, and
   wherein the combination of (A) and (B) has a synergistic effect and are present in effective amounts.

2. The pharmaceutical composition according to claim 1, wherein the agents are one or more agents selected from the group consisting of fluconazole, voriconazole, itraconazole, ketoconazole, amphotericin B, micafungin, and flucytosine.

3. The pharmaceutical composition according to claim 1, wherein the agent is one or more agents selected from the group consisting of fluconazole, voriconazole, itraconazole, and ketoconazole.

4. The pharmaceutical composition according to claim 1, wherein the agent is amphotericin B.

5. The pharmaceutical composition according to claim 1, wherein the agent is micafungin.

6. The pharmaceutical composition according to claim 1, wherein the agent is flucytosine.

7. The pharmaceutical composition according to claim 1, wherein the agent is one or more agents selected from the group consisting of fluconazole, voriconazole, and itraconazole.

8. The pharmaceutical composition according to claim 1, wherein the agent is tacrolimus.

9. The pharmaceutical composition according to claim 1, wherein the fungal infection is caused by a fungal pathogen selected from *Candida albicans, Cryptococcus neoformans,* and *Aspergillus fumigatus.*

10. A method of treating a fungal infection caused by a fungal pathogen in a subject in need thereof comprising administering a composition having a synergist effect and comprising an effective amount of
- (A) 4-{3-[4-(3-{4-[amino(imino)methyl] phenoxy}propyl)-1-piperidinyl]propoxy}benzamidine and
- (B) one or more agents selected from the group consisting of fluconazole, voriconazole, itraconazole, ketoconazole, amphotericin B, micafungin, flucytosine, and tacrolimus, and wherein the fungal infection is caused by a fungal pathogen selected from *Candida albicans, Cryptococcus neoformans, Aspergillus fumigatus,* and *Malassezia furfur.*

11. The method according to claim 10, wherein the agents are one or more agents selected from the group consisting of fluconazole, voriconazole, itraconazole, ketoconazole, amphotericin B, micafungin, and flucytosine.

12. The method according to claim 10, wherein the agent is one or more agents selected from the group consisting of fluconazole, voriconazole, itraconazole, and ketoconazole.

13. The method according to claim 10, wherein the agent is amphotericin B.

14. The method according to claim 10, wherein the agent is micafungin.

15. The method according to claim 10, wherein the agent is flucytosine.

16. The method according to claim 10, wherein the agent is one or more agents selected from the group consisting of fluconazole, voriconazole, and itraconazole.

17. The method according to claim 10, wherein the agent is tacrolimus.

18. The method according to claim 10, wherein the fungal infection is caused by a fungal pathogen selected from *Candida albicans, Cryptococcus neoformans,* and *Aspergillus fumigatus.*

19. The pharmaceutical composition according to claim 1, wherein the fungal infection is caused by *Candida.*

20. The method according to claim 10, wherein the fungal infection is caused by *Candida.*

* * * * *